US00PP23021P3

(12) United States Plant Patent
Perl et al.

(10) Patent No.: US PP23,021 P3
(45) Date of Patent: Sep. 11, 2012

(54) GRAPEVINE NAMED 'BLACK GLORY'

(50) Latin Name: ***Vitis vinifera* L.**
Varietal Denomination: BLACK GLORY

(75) Inventors: Avichai Perl, Rishon Lezion (IL); Nachman Sahar, Rehovot (IL); Oded Degani, Moshav Sde Moshe (IL); Tatiana Okun, Rehovot (IL); Arie Sarfian, Nes-Ziona (IL); Hanan Bazak, Carmei Yossef (IL); Refael Eliassi, Neve Yamin (IL); Ahuva Daos, Ganey Hmoshava Mazkeret Batia (IL)

(73) Assignee: State of Israel, Ministry of Agriculture & Rural Development, Agricultural Research Organization, Bet Dagan (IL)

( * ) Notice: Subject to any disclaimer, the term of this patent is extended or adjusted under 35 U.S.C. 154(b) by 0 days.

(21) Appl. No.: 12/929,130

(22) Filed: Jan. 3, 2011

(65) Prior Publication Data

US 2011/0277195 P1 Nov. 10, 2011

(30) Foreign Application Priority Data

Jan. 4, 2010 (IL) ..... PBR 4234

(51) Int. Cl.
*A01H 5/00* (2006.01)

(52) U.S. Cl. ..... Plt./205

(58) Field of Classification Search ..... Plt./205
See application file for complete search history.

*Primary Examiner* — Annette Para
(74) *Attorney, Agent, or Firm* — Foley & Lardner LLP

(57) ABSTRACT

This invention relates to a new and distinct variety of a grapevine named 'BLACK GLORY'. The new mid-late ripening, very fertile grapevine variety is particularly characterized by a pear-shaped, black skinned berry, having a pleasant muscat flavor.

6 Drawing Sheets

Botanical name of the genus and species of the plant claimed: *Vitis vinifera* L.

Variety denomination: 'BLACK GLORY'.

PRIORITY CLAIM

This application claims priority under 35 U.S.C. §119(f) of the Israeli Plant Breeders' Rights Application No. 4234 filed Jan. 4, 2010.

BACKGROUND OF THE INVENTION

The present invention relates to a new and distinct grapevine variety, botanically known as *Vitis vinifera* L., and hereinafter referred to by its variety denomination 'BLACK GLORY'.

The new grapevine 'BLACK GLORY' is a product of a controlled breeding program conducted by the inventors, Avichai Perl, Nachman Sahar, Oded Degani, Tatiana Okun, Arie Sarfian, Hanan Bazak, Refael Eliassi and Ahuva Daos at The Volcani Center, located in Bet Dagan, Israel. The objective of the breeding program was to develop a new mid-late ripening, very fertile grapevine variety particularly characterized by a pear-shaped, black skinned berry, having a pleasant muscat flavor.

The new grapevine 'BLACK GLORY' originated from a cross made by the inventors in 1999 at The Volcani Center. The female or seed parent is the grapevine *Vitis vinifera* L. indicated as 'ARO 28' (unpatented), in the inventors' collection located in Bet Dagan, Israel and the male or pollen parent is the grapevine *Vitis vinifera* L. indicated as 'ARO 6195' (unpatented) in the inventors' collection. The new grapevine 'BLACK GLORY' was observed and selected by the inventors within the progeny of the stated cross in a controlled environment in 2001 at The Volcani Center.

Asexual propagation of the new grapevine variety by bud grafting was first performed in January 2002 at The Volcani Center, and has demonstrated that the combination of characteristics as herein disclosed for the new variety is firmly fixed and retained through successive generations of asexual propagation. The new cultivar propagates true-to-type.

SUMMARY OF THE INVENTION

'BLACK GLORY' can be grown in various climates and growing conditions. The variety produces and maintains a strong vigorous plant and consistent fruit production from August through September in Bet Dagan, Israel.

The following traits have been repeatedly observed and are determined to be characteristics of 'BLACK GLORY', which in combination distinguish this grapevine as a new, unique and distinct variety.

1. Very fertile;
2. Mid late ripening;
3. Pear shaped berry;
4. Black skinned berry; and
5. Pleasant muscat flavor.

Plants of the new grapevine 'BLACK GLORY' differ from plants of the parents, *Vitis vinifera* L. 'ARO 28' (unpatented) and *Vitis vinifera* L. 'ARO 6195' (unpatented), in the following characteristics described in Table 1.

TABLE 1

Comparison with parent varieties.

| Characteristic | New Variety 'BLACK GLORY' | Female Parent 'ARO 28' (unpatented) | Male Parent 'ARO 6195' (unpatented) |
|---|---|---|---|
| Berry shape | Pear shaped | oval | broad elliptic |
| Berry color of skin | blackish purple | blue-black | yellow green |
| Berry thickness of skin | thin | | thin |
| Seeds | absent | | absent |

Of the many commercial varieties known to the present inventors, the most similar to the new grapevine 'BLACK GLORY' are *Vitis vinifera* L. 'MIDNIGHT BEAUTY' (U.S. Plant Pat. No. 10,434) and *Vitis vinifera* L. 'JET BLACK' (registered for Israeli Plant Breeders' Rights No. 1465), which differ from the new grapevine 'BLACK GLORY' in the characteristics described in Table 2:

TABLE 2

Comparison with most similar variety.

| Characteristic | New Variety 'BLACK GLORY' | Comparison Variety 'MIDNIGHT BEAUTY' (patented) | Comparison Variety 'JET BLACK' (registered) |
|---|---|---|---|
| Berry shape | obovate | cylinderical to ovate | nearly round |
| Berry color of skin | blackish purple | dark red-violet | blue-black |
| Berry thickness of skin | thin | thick | thick |
| Seeds | absent | absent | rudimentary |

BRIEF DESCRIPTION OF THE PHOTOGRAPHS

The accompanying photographs illustrate the overall appearance of the new grapevine 'BLACK GLORY' showing the colors as true as is reasonably possible with colored reproductions of this type. Colors in the photographs may differ slightly from the color values cited in the detailed morphological description, which accurately describe the color of 'BLACK GLORY'.

DETAILED MORPHOLOGICAL DESCRIPTION

Figure 1:
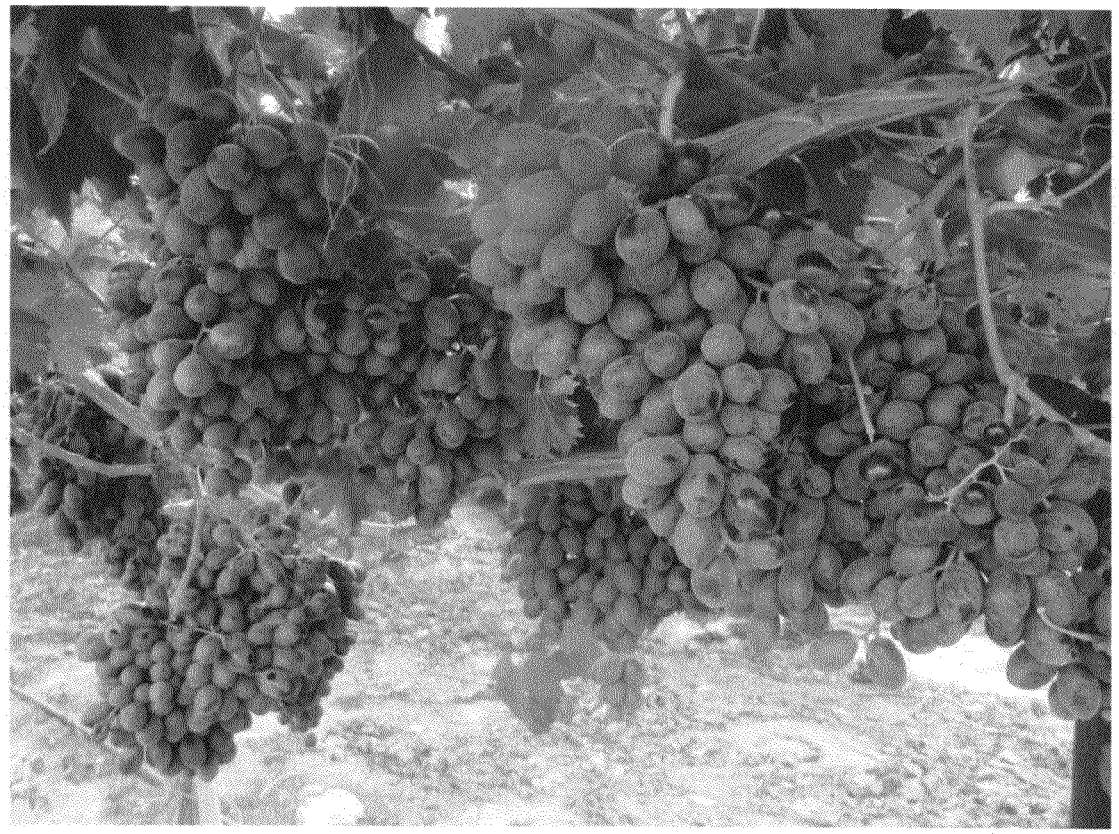
FIG. 1 shows a typical bunch of 'BLACK GLORY' on the plant.
Figure 2:
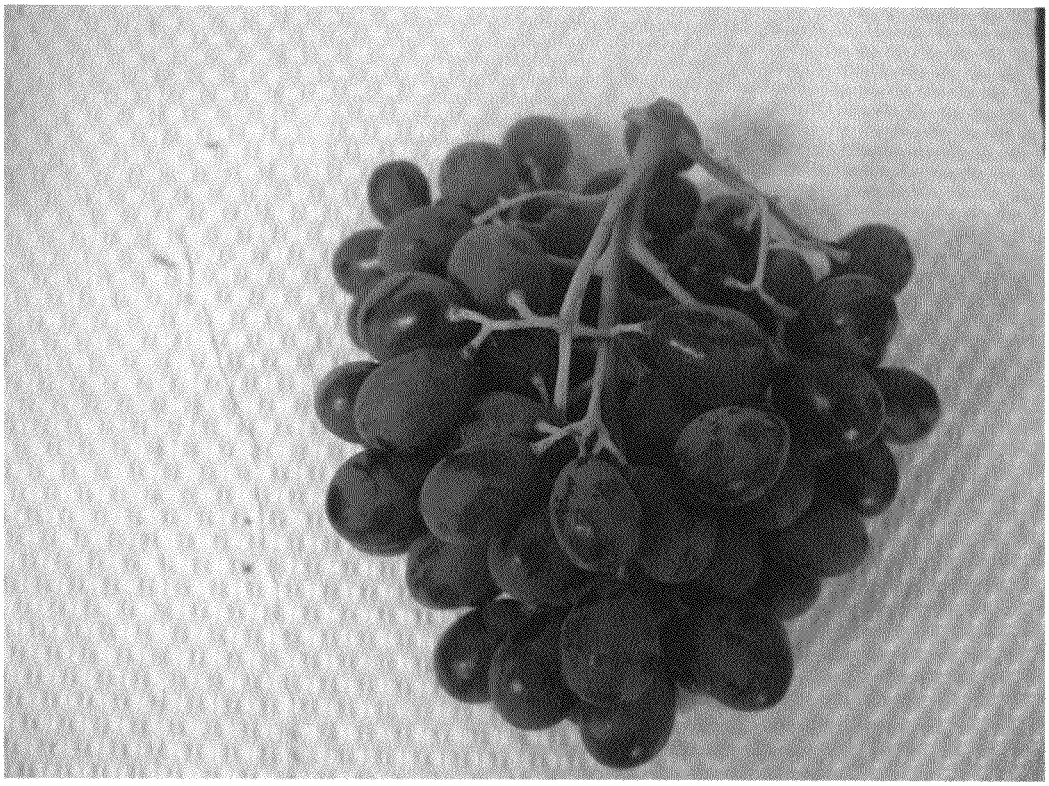
FIG. 2 shows a typical bunch of 'BLACK GLORY'.
Figure 3:
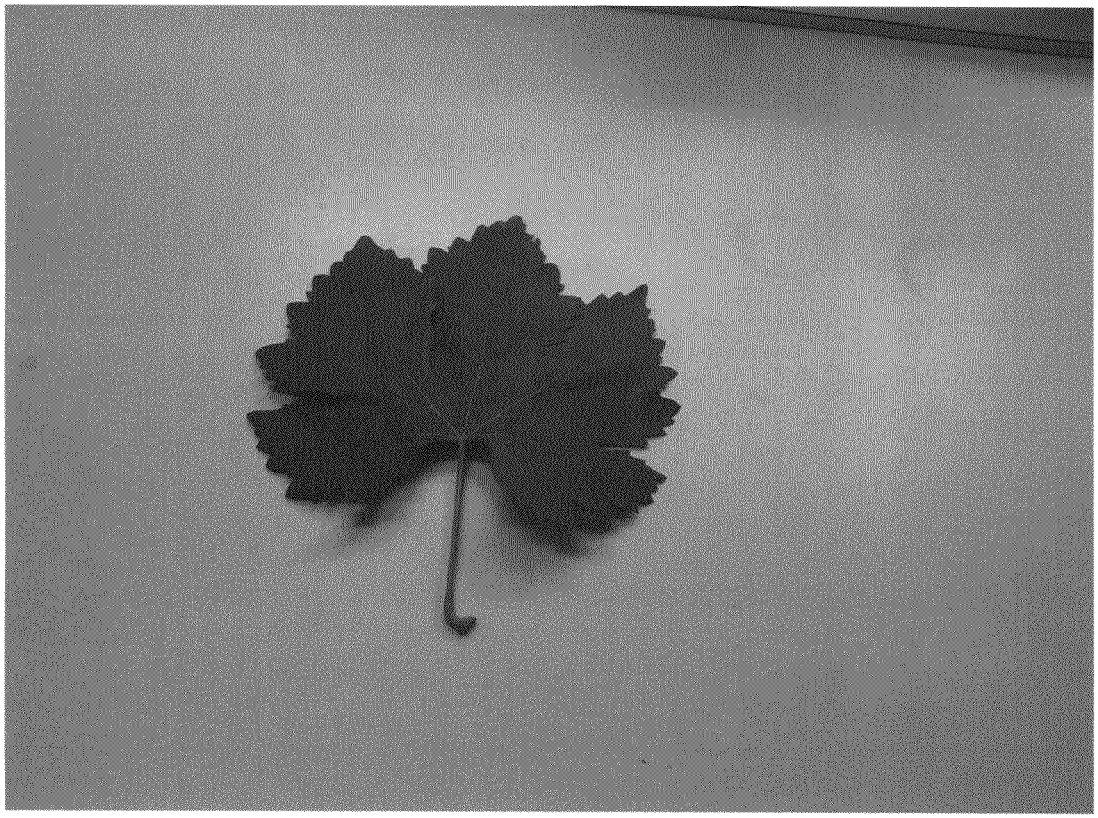
FIG. 3 shows a typical mature leaf of 'BLACK GLORY'.
Figure 4:
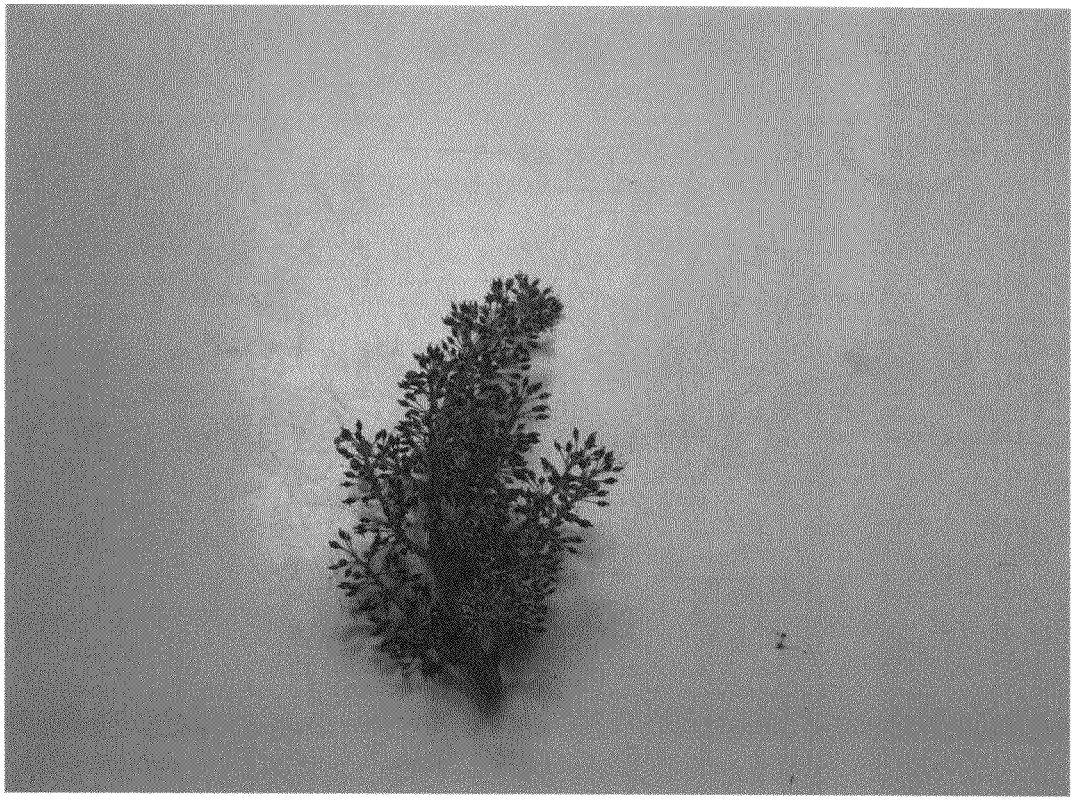
FIG. 4 shows a typical inflorescence of 'BLACK GLORY'.
Figure 5:
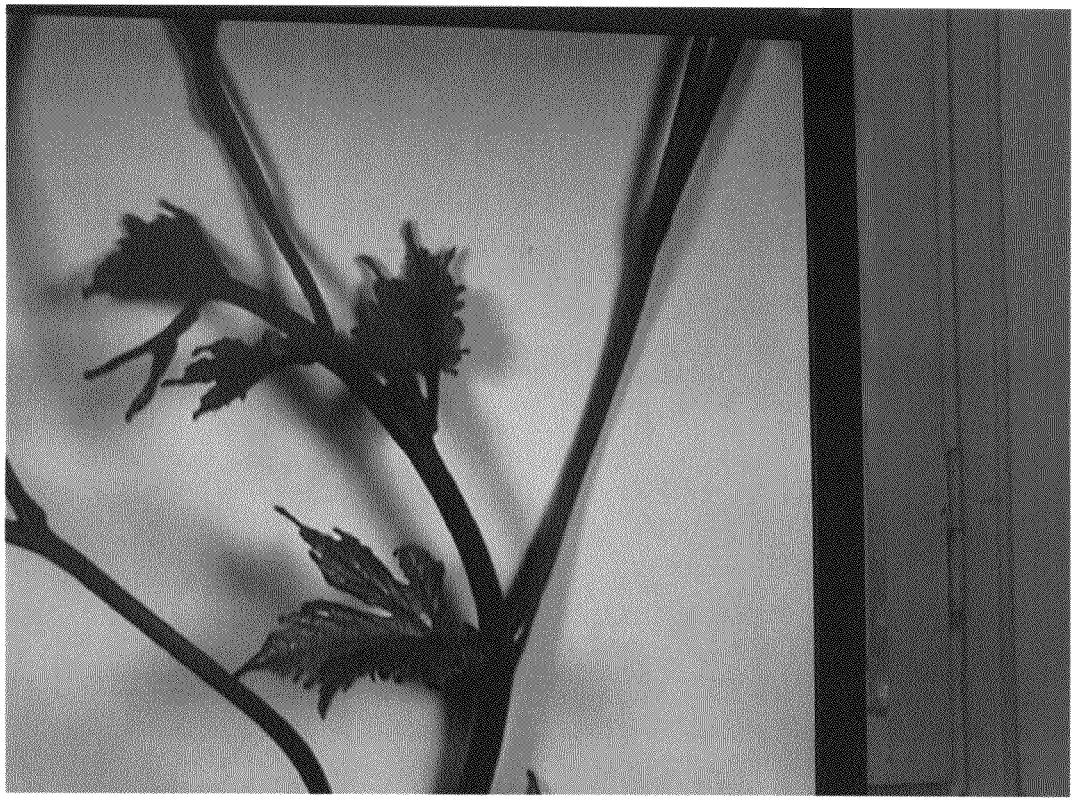
FIG. 5 shows a typical growth tip of 'BLACK GLORY'.
Figure 6:
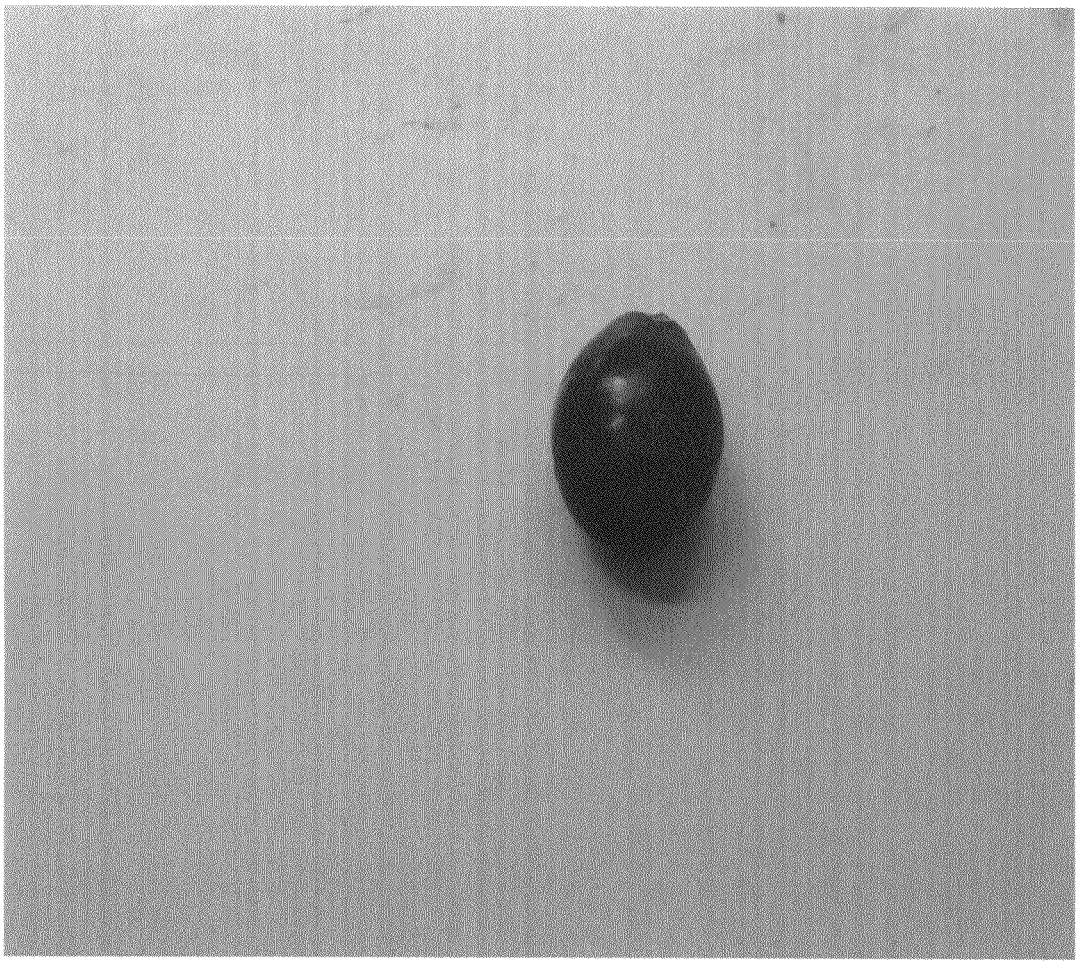
FIG. 6 shows a typical berry of 'BLACK GLORY'.

The new *Vitis vinifera* L. 'BLACK GLORY' has not been observed under all possible environmental conditions. The phenotypical descriptions and color designations stated for the new variety may vary, depending on variations in environmental factors, including weather (temperature, humidity and light intensity), day length, soil type, location and cultural conditions, without any change in the genotype of the grapevine.

The following description of 'BLACK GLORY' unless otherwise noted, is based on observations and measurements taken during 2010 and 2011 at The Volcani Center, on plants grown in the vineyard located in Bet Dagan, Israel under conditions which closely approximate those generally used in commercial practice. The described plants were grafted on 'Richter110' (unpatented) and planted at a distance of 1.5 m in sandy red loam soil at an elevation of about 30 meters above sea level with drip-irrigation up to 40 $m^3$ per hectare in the peak season in the summer and Shefer 737+micro-elements 1.5 ltr. fertilizers in each 5 $m^3$ of water. Average annual rainfall is about 550 mm, with an average of 350 mm rainfall in winter (December through February). Mean diurnal minimum temperature in January is 7.2° C., and mean diurnal maximum temperature in July is 30.8° C.

Unless otherwise stated, the detailed morphological description includes observations, measurements and values based on six-year-old 'BLACK GLORY' plants grown in the vineyard at The Volcani Center, located in Bet Dagan, Israel from 2010 to 2011. Quantified measurements are expressed as an average of measurements taken from a number of plants of 'BLACK GLORY'. The measurements of any individual plant, or any group of plants, of the new variety may vary from the stated average.

Color references are made to The Royal Horticultural Society Colour Chart (R.H.S.), 1986 edition, except where general colors of ordinary significance are used. Color values were taken under daylight conditions in full sunlight in Bet Dagan, Israel.

All of the plants of 'BLACK GLORY', insofar as they have been observed, have been consistent in all the characteristics described below.

Classification:

*Botanical.*—*Vitis vinifera* L.

Parentage:

*Female or seed parent.*—*Vitis vinifera* L. 'ARO 28' (unpatented).

*Male or pollen parent.*—*Vitis vinifera* L. 'ARO 6195' (unpatented).

Propagation: Grafting onto 'Richter110' (unpatented), Interspecific Cross, *V. berlandieri* Planch×*V. rupestris* Scheele.

Growing conditions:

*Light intensities*.—Full sunlight.

*Temperature*.—Bet Dagan — 30 meters above sea level.

| | January | February | March | April | May | June |
|---|---|---|---|---|---|---|
| Mean maximum air temperature (° C.) | 17.8 | 18.1 | 20.1 | 24.5 | 27 | 29.2 |
| Mean minimum air temperature (° C.) | 7.2 | 7.1 | 8.8 | 11.5 | 14.6 | 17.9 |
| Mean rainfall (mm) | 140.5 | 96.9 | 66.1 | 17.5 | 2.2 | — |

| | July | August | September | October | November | December |
|---|---|---|---|---|---|---|
| Mean maximum air temperature (° C.) | 30.8 | 31.2 | 30.4 | 28.3 | 24.1 | 19.7 |
| Mean minimum air temperature (° C.) | 20.6 | 21.2 | 19.4 | 16 | 11.8 | 8.6 |
| Mean rainfall (mm) | — | — | 0.4 | 20.4 | 76.2 | 130.3 |

*Fertilization*.—A balanced fertilizer with level of Shefer 737+microelements 1.5 ltr. in each 5 $m^3$ of water.
*Growth regulators*.—None applied.
*Pruning*.—As in commercial practice.
*Training*.—Y trailing cordon.

TABLE OF CHARACTERISTICS

Plant:
*Time of vegetative bud burst*.—Mid March.
Young shoot:
*Openness of tip*.—Closed.
*Density of prostrate hairs on tip*.—Medium.
*Anthocyanin coloration of prostrate hairs on tip*.—Very weak.
*Green color*.—Green RHS 144 A.
*Green color of upper side of undeveloped leaf blade*.—Medium green RHS 146 A.
*Green color of lower side of undeveloped leaf blade*.—Medium green RHS 146 B.
*Anthocyanin coloration*.—Weak.
Young leaf:
*Density of hairs between main veins on lower side of blade*.—Sparse.
*Glossiness of upper side*.—Strong.
*Glossiness of lower side*.—Weak.
Shoot:
*Length of internode*.—9-13 cm.
*Thickness of internode*.—About 8 mm.
*Color of dorsal side of internode*.—Green RHS 144 B.
*Anthocyanin coloration of dorsal side of internode*.—Brown red RHS 178 B.
*Distribution of anthocyanin coloration of dorsal side of internode*.—Blushed and striped.
*Color of ventral side of internode*.—Green RHS 144 B.
*Anthocyanin coloration of ventral side of internode*.—Absent.
*Distribution of anthocyanin coloration of ventral side of internode*.—Not relevant.
*Erect hairs on internodes*.—Absent.
*Height of node*.—About 2 cm.
*Swelling at node*.—1-2 mm.
*Diameter of node*.—10-15 mm.
*Color of dorsal side of node*.—Green RHS 144 B.
*Anthocyanin coloration of dorsal side of node*.—Brown red RHS 178 B.
*Distribution of anthocyanin coloration of dorsal side of node*.—Blushed and striped.
*Color of ventral side of node*.—Green RHS 144 B.
*Anthocyanin coloration of ventral side of node*.—Absent.
*Distribution of anthocyanin coloration of ventral side of node*.—Not relevant.
*Pubescence of node*.—Absent.
*Length of tendril*.—21-32 cm.
*Diameter of tendril at base*.—About 2 mm.
*Diameter of tendril at tip*.—Upto 1 mm.
*Pubescence of tendril*.—Absent.
*Number of bifurcations per tendril*.—2-4.
*Color of tendril*.—Yellowish green RHS 145 A.
*Anthocyanin coloration of tendril*.—Slightly blushed at lower part.
*Number of consecutive tendrils*.—Non continuous.
Inflorescence:
*Length*.—11-15 cm.
*Maximum diameter*.—3-4 cm.
*No. of side branches*.—About 11.
*Attitude of side branches*.—Semi upright.
*Length of longest side branch*.—3-6 cm.
*Thickness of main axis*.—4-5 cm.
*Green color of main axis*.—Green RHS 146 C.
*Anthocyanin coloration of main axis*.—Absent.
*Pubescence of main axis*.—Weak.
Flower:
*Sexual organs*.—Fully developed stamen and fully developed gynoecium.
Pedicel:
*Length*.—3-4 mm.
*Thickness*.—Less than 1 mm.
*Green color*.—Green RHS 146 C.
*Pubescence*.—Weak.
Stamen:
*Number*.—Five.
*Length of filament*.—2-3 mm.
*Thickness of filament*.—Minuscule.
*Pubescence of filament*.—Absent.
*Surface*.—Smooth.
*Color*.—Green RHS 145 C.
Anther:
*Shape*.—Transverse elliptic.
*Length*.—Minuscule.
*Color*.—Light green RHS 145 C.
Pollen:
*Color*.—Yellow RHS 150 C.
Ovary:
*Shape*.—Obovate, riged.
*Color*.—Green RHS 146 B.
*Length*.—2-3 mm.
*Diameter*.—2-3 mm.
*Surface*.—Smooth.
Style:
*Length*.—Minuscule.
Stigma:
*Size*.—Minuscule.
*Color*.—Yellow green RHS 146 D.
Mature leaf:
*Blade length*.—12-16 cm.
*Blade width*.—16-18 cm.
*Shape of blade*.—Pentagonal.
*Green color of upper side*.—Dark green RHS 147 A.
*Green color of lower side*.—Dark green between RHS 146 A and 146 B.
*Glossiness of upper side*.—Medium.
*Glossiness of lower side*.—Absent.
*Profile in cross section*.—Flat.
*Blistering of upper side*.—Weak.
*Number of lobes*.—Five.
*Central lobe length*.—About 9 cm.
*Central lobe width*.—About 8 cm.
*Upper, side lobe length*.—About 7 cm.
*Upper, side lobe width*.—About 6 cm.
*Pubescence of veins on upper side*.—Weak.
*Pubescence of veins on lower side*.—Weak.
*Green color of veins on upper side*.—Green RHS 145 A.
*Green color of veins on lower side*.—Yellow green RHS 145 B.
*Anthocyanin coloration of veins on upper side*.—Absent.

*Anthocyanin coloration of veins on lower side.*—Absent.
*Depth of upper lateral sinus.*—Deep.
*Arrangement of lobes of upper leaf sinus.*—Slightly overlapping.
*Arrangement of lobes of petiole sinus.*—Very open.
*Petiole sinus limited by veins.*—Absent.
*Length of distal tooth.*—9-11 mm.
*Width of distal tooth.*—9-10 mm.
*Ratio length/width of distal tooth.*—Large.
*Shape of tooth.*—Straight on both sides.
*Anthocyanin coloration of main veins on upper side of blade.*—Absent.
*Density of hairs between veins on upper side of blade.*—Very sparse.
*Density of hairs between veins on lower side of blade.*—None.
*Length of petiole compared to main vein.*—Much shorter.
*Length of petiole.*—5-8 cm.
*Petiole thickness.*—2-3 mm.

Petiole:
*Green color of upper side.*—Green yellow RHS 145 A.
*Anthocyanin coloration of upper side.*—Red between RHS 59 C and 59 D.
*Green color of lower side.*—Green yellow RHS 145 A.
*Anthocyanin coloration of lower side.*—Red between RHS 59 C and 59 D.
*Pubescence.*—Very weak.

Fruit:
*Time of beginning of berry ripening.*—Medium.

Bunch:
*Length (peduncle included).*—15-20 cm.
*Maximum diameter.*—8-11 cm.
*Weight.*—Medium.
*General shape.*—Narrow spindle.
*Peduncle length.*—3-4 cm.
*Peduncle thickness.*—4-6 mm.
*Peduncle color.*—Green RHS 144 B with medium anthocyanin coloration, brown red RHS 184 B.
*Peduncle lignification.*—Absent.
*Density.*—Medium.

Pedicel:
*Length.*—8-10 mm.
*Thickness.*—About 2 mm.
*Color.*—Yellowish green RHS 144 B.

Berry:
*Detachment.*—Easy.
*Length.*—27-33 mm.
*Diameter.*—18-22 mm.
*Weight.*—.
*Shape in profile.*—Basically obovate, slightly reminding pear shape.
*Shape in cross section.*—Rounded.
*Depression at distal end.*—Absent.
*Color of skin (without bloom).*—Blackish purple RHS 187 A.
*Amount of bloom.*—Absent.
*Surface.*—Smooth.
*Thickness of skin.*—Thin.
*Adherence of skin to flesh.*—Strong.
*Flesh color.*—Light green RHS 144 C.
*Flesh anthocyanin coloration.*—Weak.
*Firmness of flesh.*—Firm.
*Juiciness of flesh.*—Low.
*Particular flavor.*—Slight Muscat flavor at full ripening.
*Formation of seeds.*—None.

Woody shoot:
*Length of node.*—Variable.
*Main color (without bloom).*—Very dark brown between RHS 200 C and 200 D.
*Relief of surface.*—Rough.
*Shape in cross section.*—Ribbed.
*Diameter.*—About 13 mm.
*Lenticels.*—Not visible.

Usage: Table grape.

Fruit keeping quality: The fruit has a shelf life of about 12 weeks without losing firmness and juiciness.

Disease\pest resistance: No atypical resistance has been noted.

What is claimed is:

1. A new and distinct grapevine variety, referred to as 'BLACK GLORY', as herein described and illustrated by the characteristics set forth above.

* * * * *